United States Patent
Bellmann et al.

(10) Patent No.: US 6,605,295 B1
(45) Date of Patent: Aug. 12, 2003

(54) STORAGE-STABLE OPHTHALMIC COMPOSITIONS COMPRISING DICLOFENAC AND OFLOXACIN

(75) Inventors: Gunther Bellmann, Berlin (DE); Gudrun Claus-Herz, Berlin (DE); Christoph Kessler, Berlin (DE)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 09/462,731

(22) PCT Filed: Jul. 9, 1998

(86) PCT No.: PCT/EP98/04267

§ 371 (c)(1), (2), (4) Date: Mar. 20, 2000

(87) PCT Pub. No.: WO99/02130

PCT Pub. Date: Jan. 21, 1999

(30) Foreign Application Priority Data

Jul. 11, 1997 (DE) .......................................... 197 29 879

(51) Int. Cl.$^7$ .................................................. A61F 2/00
(52) U.S. Cl. ....................... 424/427; 514/912; 514/914
(58) Field of Search ................................ 424/427, 450, 424/78.04; 514/567, 230.2, 413, 912, 914

(56) References Cited

U.S. PATENT DOCUMENTS 4,551,456 A * 11/1985 Katz .......................... 514/254
5,679,665 A * 10/1997 Bergamini et al. .......... 514/171

FOREIGN PATENT DOCUMENTS

| EP | 0 242 328 A2 | 10/1987 | ......... A61K/31/195 |
|----|--------------|---------|----------------------|
| EP | 0 274 714 A1 | 7/1988 | ......... A61K/31/535 |
| EP | 0 275 515 A1 | 7/1988 | ......... A61K/31/535 |
| EP | 0 306 984 A1 | 3/1989 | ............ A61K/9/06 |
| EP | 0 711 546 A1 | 5/1996 | ............ A61K/9/00 |
| ES | 2 065 846 | 2/1995 | ........... A61K/31/57 |
| WO | WO 89/06964 | 8/1989 | ......... A61K/31/74 |
| WO | WO 90/01933 | 3/1990 | ......... A61K/31/56 |

OTHER PUBLICATIONS

"Hagers Handbuch", der pharmazeutischen Praxis, 5$^{th}$ edition, pp. 639–649.

Chemical Abstract, 63–Pharmaceuticals, vol. 122, Jun. 26, 1995, pp. 581.

* cited by examiner

Primary Examiner—James M. Spear
Assistant Examiner—Blessing Fubara
(74) Attorney, Agent, or Firm—John E. Thomas

(57) ABSTRACT

The invention relates to stable ophthalmic preparations including the penetrant antiphlogistic diclofenac or salts thereof and the penetrant antibiotic ofloxacin present in the form of the racemate, an enantiomer, particularly levofloxacin, or the corresponding hydrochloride thereof. The preparations may be used for treating eye infections and/or inflammations and for preventing infections before and after eye surgery.

12 Claims, No Drawings

STORAGE-STABLE OPHTHALMIC COMPOSITIONS COMPRISING DICLOFENAC AND OFLOXACIN

This application is a 371 of PCT/EP98/04267 filed Jul. 9, 1998.

The invention pertains to storage-stable ophthalmic compositions containing diclofenac or its salts and ofloxacin in the form of a racemate, one of its enantiomers, in particular of levofloxacin, or of the corresponding hydrochloride. In addition, the invention pertains to the use of such ophthalmic compositions to treat eye inflammations and/or infections as well as to the prophylaxis of infection before and after eye operations.

Both the individual as well as the combined administration of antibiotics and antiphlogistics for the simultaneous treatment of inflammations and infections of the front section of the eye have been known for a long time. In this regard, the administration of appropriate composition preparations has proven especially advantageous.

It must be ensured with such composition preparations that the components do not affect one another negatively in so far as their effectiveness and stability are concerned or even enter into chemical reactions with one another which could result in undesirable by-products.

Ophthalmic composition preparations made of antibiotics and steroidal antiphlogistics which meet these criteria are disclosed in PCT application WO90/01933. Ofloxacin in combination with dexamethasone or rimexolon, among others, is mentioned as an active ingredient. Although the compatibility of the components and the storage stability of these compositions are satisfactory, they are tainted with the known disadvantages caused by the steroid components, such as an increase in intraocular pressure. In addition, dexamethasone is only a weakly penetrating antiphlogistic.

In order to overcome the disadvantages of known composition preparations caused bythe steroid components, the Spanishpatent specification ES 2065846 proposed combining a non-steroidal antiphlogistic with an antibiotic from the gyrase inhibitor group instead of a steroidal antiphlogistic. Ophthalmic suspensions and ointments containing the active-ingredient combinations clobetason/lomefloxacin, fluorometholon/norfloxacin, dexamethasone/ciprofloxacin, and indomethacin/norfloxacin are given as examples.

European patent application EP 0711546 discloses composition preparations for ophthalmology and otology which include the non-steroidal antiphlogistic diclofenac or its salts and the antibiotic tobramycin. The formulations described have substantial stability problems attributable to the poor solubility of diclofenac, on the one hand, and to chemical interactions between the active ingredients, on the other. It was possible to overcome the stability problems observed through careful adjustment of the active-ingredient concentrations and of the pH-value by using suitable solubilizers. A disadvantage of this composition is to be found in the fact that tobramycin cannot penetrate into the eye; therefore, it is suitable solely to treat superficial infections.

From a therapeutic point of view, an ophthalmic composition preparation made from a penetrating antiphlogistic and a penetrating antibiotic is desirable. Diclofenac or its salts and ofloxacin in the form of its racemate, one of its enantiomers, especially of levofloxacin, or of the corresponding hydrochloride, would be considered suitable active ingredients in this case.

During the first fundamental studies on this invention it was discovered that in formulating a composition medication with the active ingredients diclofenac and ofloxacin, unexpected stability problems occur in such a way that a decomposition product of ofloxacin, ofloxacin-N-oxide, is produced to a greater degree than is the case with ofloxacin in monopreparations. After a storage period of only 6 months, 2% ofloxacin-N-oxide is produced where diclofenac is present, whereas with pure solutions of ofloxacin, i.e. in the absence of diclofenac, the oxide content is less than 0.2% even after a long storage period.

The objective of this invention is to make available a stable composition preparation containing diclofenac or its salts and ofloxacin in the form of its racemate or one of its enantiomers, especially of levofloxacin, or of the corresponding hydrochloride, which can be used to treat eye inflammations and/or infections as well as a prophylaxis against infection before and after eye operations.

In accordance with the invention, the achievement of this objective is made possible through the features of the independent claims.

The dependent claims define advantageous forms of the invention.

Surprisingly, it was established that the formation of ofloxacin-N-oxide or levofloxacin-N-oxide respectively, which is described above, can be restrained through the use of antioxidation agents normally used in ophthalmic preparations.

A stable pH-value greater than 7 is to be maintained to keep the diclofenac in solution. The pH-value of ophthalmic preparations is normally adjusted by means of buffer systems.

In this case, however, it was observed that where solutions containing diclofenac and ofloxacin were buffered, precipitates were produced during the storage period, even where an oxidation agent was present, these precipitates presumably being attributable to the high salt concentration of the buffered system. These precipitates could not be prevented by adding the usual solubilizers, either.

In accordance with the invention, it was now found that stable composition preparations containing the active ingredient diclofenac or its salts and ofloxacin in the form of its racemate, one of its enantiomers, or of the corresponding hydrochloride, can be obtained by adding the usual antioxidants and doing without a buffer system, i.e. the pH-value is adjusted solely with acids or alkalis.

The inventive formulations contain 0.001–0.15% by weight, preferably 0.01–0.13% by weight, by preference 0.08–0.12% by weight, diclofenac or its salts and 0.001–0.5% by weight, preferably 0.01–0.35% by weight, by preference 0.1–0.3% by weight, ofloxacin in the form of its racemate, one of its enantiomers, especially of levofloxacin, or of the corresponding hydrochloride.

The inventive compositions contain ascorbic acid, citric acid, tartaric acid, sodium sulphite, orsodium disulphite in quantities of 0.001–0.02% by weight, preferably 0.005–0.015% by weight, by preference 0.008–0.012% by weight, as suitable antioxidants. In a formulation which is especially preferred, the inventive compositions contain sodium disulphite in concentrations between 0.008 and 0.012% by weight.

HCl and NaOH are preferably used to adjust the pH-value. The inventive compositions may contain normal solubilizers, like povidone, etc. in concentrations of 0–5% by weight, preferably 2–4% by weight and by preference 2.5–3.5% by weight, and/or polysorbate, etc. in a concentration of 0–2% by weight, preferably 0.1–1% by weight and by preference 0.3–0.7% by weight.

The inventive compositions may contain the following as further normal additives:

isotonization agents, like sodium chloride in quantities of 0–5% by weight, preferably 0.3–2% by weight, by preference 0.5–1.25% by weight, or sorbitol in quantities of 0–10% by weight, preferably 2–6% by weight, by preference 3–5% by weight;

chelating agents, like EDTA or its sodium salt in quantities of 0–0.002% by weight, preferably 0.0008–0.0012% by weight;

preservatives, like benzalkonium chloride in quantities of 0–1.0% by weight, preferably 0.01–0.5% by weight, by preference 0.02–0.04% by weight.

The inventive formulations may be formulated as eyedrops, suspensions, ointments, or gels. The formulation as eyedrops is especially preferred.

The following embodiments serve only to explain the invention and do not represent any kind of restriction.

EXAMPLE 1

Batch size: 20 l

| Components | Quantity |
| --- | --- |
| Diclofenac-sodium | 0.020 kg |
| Ofloxacin | 0.060 kg |
| Kollidon 25 | 0.600 kg |
| Sodium disulphite | 0.002 kg |
| Sodium chloride | 0.150 kg |
| 1 N HCl to adjust the pH-value | |
| 1 N NaOh to adjust the pH-value | |
| Water | 19.404 kg |

EXAMPLE 2

Batch size: 20 l

| Components | Quantity |
| --- | --- |
| Diclofenac-sodium | 0.020 kg |
| Levofloxacin | 0.060 kg |
| Sodium edetate | 0.002 kg |
| Kollidon 25 | 0.600 kg |
| Sodium disulphite | 0.002 kg |
| Sodium chloride | 0.150 kg |
| Polysorbate | 0.100 kg |
| 1 N HCl to adjust the pH-value | |
| 1 N NaOH to adjust the pH-value | |
| Water | 19.304 kg |

EXAMPLE 3

Batch size: 20 l

| Components | Quantity |
| --- | --- |
| Diclofenac-sodium | 0.020 kg |
| Ofloxacin | 0.060 kg |
| Kollidon 25 | 0.600 kg |
| Sodium disulphite | 0.002 kg |
| Sorbitol | 0.800 kg |
| Polysorbate | 0.100 kg |
| 1 N HCl to adjust the pH-value | |
| 1 N NaOH to adjust the pH-value | |
| Water | 18.838 kg |

EXAMPLE 4

Batch size: 20 l

| Components | Quantity |
| --- | --- |
| Diclofenac-sodium | 0.020 kg |
| Ofloxacin | 0.060 kg |
| Kollidon 25 | 0.600 kg |
| Sodium disulphite | 0.002 kg |
| Sorbitol | 0.800 kg |
| Benzalkonium chloride | 0.006 kg |
| Polysorbate | 0.100 kg |
| 1 N HCl to adjust the pH-value | |
| 1 N NaOH to adjust the pH-value | |
| Water | 18.832 kg |

The compositions presented as examples were stable for a long period and exhibited only low ofloxacin-N-oxide contents, which did not increase during the storage period.

The stable, inventive compositions may by used to treat eye infections and/or inflammations as well as for prophylaxis against infection before and after operations.

The results of various test series are compared in the following Table I.

TABLE I

Test Series using Various Formulations

| Formula, components in % | Test 1, Chemical designation: #950501 #950502 #950503 | Test 2, Chemical designation: #960107 #960108 #960109 | Test 3, Chemical designation: #970201 #970202 #970203 | Test 4, Chemical designation: #970817 | Test 5, Chemical designation: #971203 |
|---|---|---|---|---|---|
| Diclofenac-Na | 0.1 | 0.1 | 0.1 | 0.1 | 0.1 |
| Ofloxacin | 0.3 | 0.3 | 0.3 | 0.3 | 0.3 |
| Boric acid | 1.5 | 1.5 | — | — | — |
| Sodium tetraborate x 10 H₂O | 0.45 | 0.45 | — | — | — |
| Kollidon 25 | 3.0 | 3.0 | 3.0 | 3.0 | 3.0 |
| Tween 80 SD | 0.5 | 0.5 | — | 0.5 | 0.5 |
| Sodium disulphite | — | 0.01 | 0.01 | 0.01 | 0.01 |
| NaCl | — | — | 0.75 | 0.7 | 0.7 |
| N-oxide form t = x, 21° C., max. 1% | t = 4 months, 1.6–1.9% | t = 6 months, 0.4% | t = 3 months, 0.4% | t = 8 months, 0.48% | t = 4 months, 0.34% |
| Appearance T = x | t = 19 months solution: clear | t = 6 months precipitation | t = 3 months solution: clear | t = 8 months clear | t = 4 months clear |
| Remarks | Termination of test | Termination of test | — | — | — |

In test series 1, a composition was tested which, in addition to the active ingredients diclofenac-Na and ofloxacin, contains the buffer system boric acid/sodium tetraborate as well as the adjuvants Kollidon 25 and Tween 80 SD. Although a clear solution resulted, 1.6–1.9% ofloxacin-N-oxide was produced after only 4 months.

As test series 2 shows, it was possible to clearly restrain the production of ofloxacin-N-oxide by adding sodium disulphite; however, precipitation occurred with the compositions tested in this test series.

As test series 3, 4, and 5 show, in accordance with the invention clear solutions containing minor amounts of ofloxacin-N-oxide can be produced if sodium disulphite is added and at the same time the buffer system is not used.

What is claimed is:

1. A stable ophthalmic composition for topical administration to eye tissue comprising:
   0.001 to 0.15 weight percent of diclofenac or a salt thereof;
   0.01 to 0.5 weight percent of ofloxacin or the hydrochloride thereof;
   0.001 to 0.02 weight percent of sodium disulphite;
   0 to 5 weight percent of povidone;
   0 to 2 weight percent of polysorbate;
   0 to 5 weight percent of sodium chloride;
   0 to 10 weight percent of sorbitol;
   0 to 1.0 weight percent of benzalkonium chloride;
   0 to 0.002 weight percent of sodium edetate;
   an alkali hydroxide or acid in an amount effect to adjust a pH value of the composition to a value greater than about 7; and
   water.

2. The ophthalmic composition of claim 1, wherein the ofloxacin has the form of its racemate.

3. The ophthalmic composition of claim 1, wherein the ofloxacin is an enantiomer.

4. The ophthalmic composition of claim 3, wherein the ofloxacin enantiomer is levofloxacin.

5. The ophthalmic composition of claim 1, wherein the pH value of the composition is about 7 to about 7.4.

6. The ophthalmic composition of claim 1, comprising:
   0.001 to 0.13 weight percent of the diclofenac or its sodium salt;
   0.01 to 0.35 weight percent of the ofloxacin or the hydrochloride thereof;
   0.005 to 0.015 weight percent of sodium disulphite;
   2 to 4 weight percent of povidone;
   0.3 to 2 weight percent of sodium chloride;
   0.01 to 0.5 weight percent of benzalkonium chloride;
   0.0008 to 0.0012 weight percent of sodium edetate;
   the alkali hydroxide or acid in an amount effect to adjust the pH value; and
   water.

7. The ophthalmic composition of claim 6, comprising:
   0.08 to 0.12 weight percent of the diclofenac or its sodium salt;
   0.1 to 0.3 weight percenf the ofloxacin or the hydrochloride thereof;
   0.008 to 0.012 weight percent of sodium disulphite;
   2.5 to 3.5 weight percent of povidone;
   0.5 to 1.25 weight percent of sodium chloride;
   0.02 to 0.04 weight percent of benzalkonium chloride;
   0.0008 to 0.0012 weight percent of sodium edetate;
   the alkali hydroxide or acid in an amount effect to adjust the pH value; and
   water.

8. The ophthalmic composition of claim 1, comprising:
   0.001 to 0.13 weight percent of the diclofenac or its sodium salt;
   0.01 to 0.35 weight percent of the ofloxacin or the hydrochloride thereof;

0.005 to 0.015 weight percent of sodium disulphite;
0.1 to 1 weight percent of polysorbate;
2 to 6 weight percent of sorbitol;
0.01 to 0.5 weight percent of benzalkonium chloride;
0.0008 to 0.0012 weight percent of sodium edetate;
the alkali hydroxide or acid in an amount effect to adjust the pH value; and
water.

9. The ophthalmic composition of claim 8, comprising:
0.08 to 0.12 weight percent of the diclofenac or its sodium salt;
0.1 to 0.3 weight percent of the ofloxacin or the hydrochloride thereof;
0.008 to 0.012 weight percent of sodium disulphite;
0.3 to 0.7 weight percent of polysorbate;
3 to 5 weight percent of sorbitol;
0.02 to 0.04 weight percent of benzalkonium chloride;
0.0008 to 0.0012 weight percent of sodium edetate;
the alkali hydroxide or acid in an amount effect to adjust the pH value; and
water.

10. A method for treatment of eye inflammations comprising administering to an eye the composition of claim 1.

11. A method for treatment of eye infections comprising administering to an eye the composition of claim 1.

12. A method for treatment of eye inflammations and infections comprising administering to an eye the composition of claim 1.

* * * * *